United States Patent [19]

Ritter et al.

[11] Patent Number: 5,236,702

[45] Date of Patent: Aug. 17, 1993

[54] COMPOSITION AND METHOD FOR BLOOD COAGULATION ON HARD BODY TISSUES

[75] Inventors: Wolfgang Ritter, Haan; Wolfgang Pittermann, Duesseldorf, both of Fed. Rep. of Germany

[73] Assignee: Henkel Kommanditgesellschaft auf Aktien, Duesseldorf, Fed. Rep. of Germany

[21] Appl. No.: 462,963

[22] Filed: Jan. 4, 1990

Related U.S. Application Data

[63] Continuation of Ser. No. 193,972, May 13, 1988, abandoned, which is a continuation-in-part of Ser. No. 700,351, Feb. 19, 1985, abandoned, which is a continuation-in-part of Ser. No. 470,075, Feb. 28, 1983, abandoned.

[30] Foreign Application Priority Data

May 15, 1987 [DE] Fed. Rep. of Germany ....... 3716302

[51] Int. Cl.$^5$ ............................................. A61K 31/74
[52] U.S. Cl. ............................ 424/78.17; 424/78.08
[58] Field of Search .......................... 424/78.17, 78.08; 560/185, 198

[56] References Cited

U.S. PATENT DOCUMENTS

| | | | |
|---|---|---|---|
| 2,362,511 | 11/1944 | Teeters | 528/519 |
| 4,010,196 | 3/1977 | Tsuk | 260/484 |
| 4,011,312 | 3/1977 | Reuter et al. | 424/78 |
| 4,393,041 | 7/1983 | Brown et al. | 424/19 |
| 4,443,430 | 4/1984 | Mattei et al. | 424/78 |
| 4,563,489 | 1/1986 | Urist | 524/21 |
| 4,645,503 | 2/1987 | Lin et al. | 623/16 |

FOREIGN PATENT DOCUMENTS 1163135  6/1989  Japan .

OTHER PUBLICATIONS

Geary J. R. Annal of Surgery vol. 132 (1950).

*Primary Examiner*—Zohreh A. Fay
*Attorney, Agent, or Firm*—Ernest G. Szoke; Wayne C. Jaeschke; Daniel S. Ortiz

[57] ABSTRACT

An improved resorbable body and tissue compatible wax useful for the mechanical coagulation of blood on bones is produced by the reaction of, for example, lactic or glycolic acids with glycerol. The reaction mixture is then purified by forming a solvent suspension and washing with isopropanol to produce a purified wax essentially free of the hydroxycarboxic acid impurity, say, less than 0.1%.

16 Claims, No Drawings

COMPOSITION AND METHOD FOR BLOOD COAGULATION ON HARD BODY TISSUES

This application is a continuation of application Ser. No. 07/193,972 filed on May 13, 1988, now abandoned, which is a continuation-in-part of application Ser. No. 06/700,351 filed on Feb. 19, 1985, now abandoned, which is a continuation-in-part of application Ser. No. 06/470,075 filed on Feb. 28, 1983, now abandoned.

BACKGROUND OF THE INVENTION

1. Field of the Invention

This invention relates to mechanical blood coagulation on endogenous hard body such as bone tissue, for example, employing improved resorbable wax compositions and methods.

2. Discussion of Relate Art

This application is a continuation-in-part of application U.S. Ser. No. 06/700,351 filed Feb. 19, 1985, which is, in turn, a continuation-in-part of application U.S. Ser. No. 06/470,075, filed Feb. 28, 1983, now abandoned.

Published German Patent application P 32 29 540.5 represents the priority document on which the above identified parent applications are based.

For mechanical blood coagulation on endogenous hard body tissues, such as bone, for example, it is customary to treat resected bone parts with bone wax. For the same reason, blocks of bone wax are also used to cover spaces filled with spongiosa.

The waxy masses used up to the present time were made, for example, of beeswax, almond oil and salicylic acid, or beeswax and isopropyl palmitate. Relevant literature includes, for example, Douglas, B. L.: Oral Surg., Vol. 6, p.1195, 1953;
Selden, H. S.: Oral Surg., Vol. 29, p. 262, 1970;
Shields, T. W.: General Thoracic Surgery, Lea and Febiger, Philadelphia, 1972; and
Wolter, D. et al.: Chirug., Vol. 46, p. 459, 1975.

In general, postoperative healing proceeds without disturbance; bacterial contamination is rare.

Commonly, however, in the case of the bone waxes used for coagulation during surgery up to the present time, coverage of the implant by granulation tissue containing abundant macrophages and giant cells is observed, see D. Wolter et al., op eit. The granulation tissue becomes fibrotic within the body with the passage of time.

Direct contact between the bone and the wax does not occur. Nonspecific foreign body reactions often take place at the spongiosa/bone wax contact zones. This inhibits the new formation of bone and promotes the development of pseudoarthroses, see Geary, I. R. et al.: Ann. Surg., Vol. 132, p. 1128, 1950 and
Howard, C. C. et al.: Clin. Orthop., Vol. 63, p. 226, 1969.

High molecular weight polymers and their use in the medical sector are known. They have fiber properties. Their tolerance and degradability have been studied in detail. Well known, for example, are synthetic filament materials, resorbable with the body, based on polyglycolic acid and polylactic acid; see for example, U.S. Pat. Nos. 3,297,033; 3,626,948; 2,668,162; 2,676,945 and 2,703,316.

Published German patent application P32 29 540.5 relate to resorbable waxes for mechanical blood coagulation on hard body tissue, more especially on bones, which consist of wax-like polyester oligomers of lower hydroxycarboxylic acids. These materials range from viscous to solid at body temperature. By virtue of their structure, these waxes are degradable by the body's own metabolic processes, the degradation rate being adjustable in known manner. The preferred waxes have average molecular weights of about 200 to 1500 and, more especially, of about 300 to 1000.

Corresponding polyester oligomers of lactic acid and/or glycolic acid are described as being particularly suitable. According to the published German patent application cited above, monofunctional and/or difunctional alcohols or carboxylic acids or carboxylic anhydrides and/or primary or secondary monoamines may be used to regulate the average molecular weight of the polyester oligomers. A definitive average molecular weight may be determined in advance in a known manner by selecting suitable mixing ratios of oxycarboxylic acids and additional monofunctional or difunctional component. It is known that the reaction products obtained are not uniform in their degree of oligomerization and still contain certain quantities of the starting components.

DESCRIPTION OF THE INVENTION

Other than in the operating examples, or where otherwise indicated, all numbers expressing quantities of ingredients or reaction conditions used herein are to be understood as modified in all instances by the term "about".

An objective of this invention is to optimize resorbable waxes for the mechanical absorption of blood on hard body tissue of the described type.

One aspect of the present invention relates to compositions which, because of their consistency, can assume the tasks previously required of a bone wax, but at the same time, as a result of their chemical structure, avoid the disadvantages of the previous bone waxes. In particular, the wax-like compositions in accordance with the present invention are physiologically safe and readily resorbable, and do not lead to the formation of toxic degradation products. In a specific embodiment of the invention, a controllable degradation of these waxy masses by endogenous degradation reactions takes place, so that nonspecific foreign body reactions and, in particular, chronic inflammations at the tissue/bone wax contact zones is avoided. In addition, as a result of the resorbability of the present compositions in accordance with the invention, uninhibited new formation of bone is promoted.

In accordance with the present invention it has been discovered that improved, resorbable, body tissue compatible waxes are produced and isolated from the reaction product of at least one hydroxycarboxylic acid and a trihydroxy alcohol or adduct of said alcohol. The trihydroxy alcohol is employed as a co-reactant to adjust the average molecular weight of the resulting polyester oligomer of a hydroxycarboxylic acid such that waxes are obtained which are viscous to solid at body temperature and which exhibit particularly improved properties.

The combination of glycerol with oligoesters of hydroxycarboxyic acids, preferably lactic acid and/or glycolic acid leads to degradable wax-like components of the type mentioned which, on implantation in living body tissue, are distinguished by particularly pronounced compatibility with the body.

Accordingly, the present invention relates to resorbable waxes for the mechanical blood coagulation on hard body tissue, more especially bone, of wax-like polyester oligomers of hydroxycarboxylic acids, especially lactic acid and/or glycolic acid which range from viscous to solid at body temperature and which are prepared using a trihydroxy alcohol or adducts thereof to regulate the average molecular weight of the polyester oligomers. The polyester oligomer waxes according to the present invention has incorporated therein at least one co-reactant moiety bound thereto in a terminal position, where the co-reactant is a trihydroxy alcohol or solvent thereof.

While glycerol is preferred, and physiologically compatible trihydroxy alcohol or adducts, such as glycerol with 1–6 moles of propylene oxide are employed.

The oligomer segments of these preferred wax compositions generally contain the structural unit:

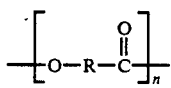

wherein R is a straight or branched chain alkyl group, an unsubstituted or alkyl substituted cycloakyl group, or an unsubstituted or alkyl substituted phenyl group, with R preferably having from 1 to 20 carbon atoms, more preferably from 2 to 10 carbon atoms, and most preferably from 2 to 6 carbon atoms; and n is an integer dependent on the selection of the R group, and is preferably chosen so that the mean molecular weight of the polyester-oligomer chain is in the range of from about 200 to about 1500, more preferably about 300 to about 1000. The desired consistency of the wax compositions is attained by careful control of the degree of oligomerization.

The above polyester-oligomer chains are obtained through oligomerization of a hydroxycarboxylic acid, or a mixture of hydroxycarboxylic acids, of the formula

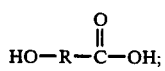

wherein R has the meaning given above.

Hydroxycarboxylic acids for use herein include glycolic acid, the isomeric lactic acids, the possibly isomeric α- or β-hydroxypropionic acids, the possibly isomeric α, β- or γ-hydroxybutyric acids, o-hydroxybenzoic acid (salicylic acid), m-hydroxybenzioc acid and/or p-hydroxybenzoic acid. Specific isomers of the acids mentioned or mixtures of the above acids can be used. When mixtures of two or more hydroxycarboxylic acids are employed, the R group defined above can have more than one structure in the polyester-oligomer chain, depending on the mixture of hydroxycarboxylic acids chosen for its preparation.

The oligomer segments of the optimized bones waxes according to this invention are preferably derived from lactic acid and/or glycolic acid. The starting material for the production of the oligomers may be the monomeric hydroxycarboxylic acids corresponding to the above definition. However, the easy-to-handle dimerization products, i.e., the lactide and/or the glycolide, will generally be used. The lactic acid dimer may be used, for example, as L-lactide or even as D,L-lactide.

Preferred waxes according to the invention are obtained where 9 to 10 mol of the monomeric glycolic acid or about 12 mol of the monomeric lactic acid are used to 1 mol glycerol.

Specific oligomerization reactions are described in the above referenced published German Patent application.

In one particularly preferred embodiment of the invention the wax-like material is at least largely freed from its content of unreacted starting components and consists essentially of the polyester oligomer. In particular, the content of unreacted hydroxycarboxylic acids is reduced to residual contents below 0.5% by weight, preferably to residual contents below 0.2% by weight, and most preferably to at or below 0.1% be weight.

Studies conducted with these materials have shown that tissue damage can be avoided particularly when it is ensured both through the production process and through subsequent purification of the degradable wax that its content of unreacted carboxyl groups is at least greatly reduced or, preferably, is substantially completely eliminated. Free carboxyl groups such a these may even be present in the reaction mixture in the absence of the molecular-weight-regulating dicarboxylic acids discussed in the above-cited published German patent application. The statistical molecular weight distribution which derives directly from the production of the waxes always leaves behind in the oligomeric reaction mixture a certain number of free carboxyl groups, which are present at least predominantly as free monomeric hydroxycarboxylic acids.

The purification of the oligomer reaction product which is initially formed is preferably carried out in accordance with the invention to remove unreacted components or reaction products having an undesirably low molecular weight. Preferably, the initially formed oligomer reaction product is mixed with a water-miscible organic solvent, for example, with a ketone such as acetone, or with an alcohol such as methanol, ethanol or the like; and the resulting suspension is introduced into a solvent which does not dissolve the desired oligomer fractions, but is an effective solvent for the unreacted and low molecular weight components of the oligomer reaction product. For example, isopropanol has been found to be a particularly suitable solvent for this second stage of the process. In one effective purification process according to this invention, the oligomerization reaction product initially formed is mixed with water-miscible solvent containing a ketone such as acetone or monohydric alcohol, such as methanol in a ratio of approximately 1:1 and intensively digested. The solids suspension formed is then introduced into several times, for example, 7 to 12 times, its volume is isopropanol and filtered off. The liquid phase is filtered under suction, washed preferably with isopropanol and then dried. A wax-like product of the desired quality substantially free from carboxyl groups is produced in this way.

The polyester oligomer waxes according to the invention are also characterized by an average molecular weight of from about 200 to 1500 and preferably of from about 300 to 1000. The resorbable waxes are paste-like to soft-spreading materials at body temperature which may be brought into a state in which they spread even more easily by brief heating to temperatures of up to about 100° C. and preferably of up to about 60° C. In this form, they are particularly suitable for the mechanical coagulation of blood by application as known per se to body tissue, for example to damaged or otherwise opened bones.

In the case of polycondensates of this type the molecular weight can be simply calculated from the components. For this purpose one first calculates the number of mols of hydroxy carboxylic acid used per mol of regulator or co-reactors such as glycerol in the product. This number is multiplied by the molecular weight of the monomeric hydroxy carboxylic acid minus 18, and the molecular weight of the regulator is added to it. In this manner one can also derive accurate molecular weights. For further details the reader is referred to: W. H. Carothers, et al., J. Am. Chem. So., Vol. 51, p. 2548, (1929) as well as P. J. Flory, *Principles of polymer Chemistry,* Cornell University Press, New York, (1953).

The molecular weights that can be calculated in this way or can be determined via end group determinations are number averages

EXAMPLES

Examples 1 to 5

Procedure for the Preparation of Oligomer Reaction Products of Glycolic Acid with Glycerol Glycolic acid and glycerol are introduced in various molar ratios as shown in Table 1 into a three-necked flask equipped with a stirrer and distillation bridge; and the mixture is rapidly heated under nitrogen to 150° C. and then over a period of 6 hours from 150° to 200° C. Most of the water of reaction if eliminated which indicates the extent of completion of the ester condensation reaction. The reaction mixture is allowed to cool to around 150° C., carefully evacuated to 10 torr and the reaction completed at 200° C./10 torr. After 30 minutes, the product is packed hot at around 150° C. The composition of the reaction mixtures and the oligomer properties are shown in Table 1.

Examples 6 to 8

Procedure of the Preparation of the Reaction Products of Glycolide with Glycerol Glycolide and glycerol were heated with stirring under nitrogen in a conventional laboratory apparatus, for 1 hour to 195° C. The reactants were then left to react for 3 hours at 195° C., and the reaction product subsequently packed while still hot. An Sn(II) chloride solution in ether was added as catalyst (7 ml of a solution of 2.5 g $SnCl_2$ in 1000 ml ether in the reaction of 3 mol glycolide with 1 mol glycerol).

Examples 9 to 16

Procedure for the Preparation of the Reaction Products of Lactide with Glycerol

In a conventional laboratory apparatus, lactide (L(−) lactid N, B of Beohringer Ingelheim) and glycerol were heated with stirring under nitrogen for 1 hour to 195° C. The reactants were then left to react for 3 hours at 195° C., and the reaction product subsequently packed while still hot. An Sn(II) chloride solution in ether was added as catalyst (7 ml of a solution of 2.5 g $SnCl_2$ in 1000 ml ether in the reaction of 3 mol lactide with 1 mole glycerol). Results are shown in Table 3.

TABLE 1

Oligohydroxycarboxylic acids from glycolic acid and glycerol

| Example | Rection Mixture Glycolic acid mol | Glycerol mol | Yield water of reaction % | Viscosity at measuring temperature | Quality |
| --- | --- | --- | --- | --- | --- |
| 1 | 8 | 1 | 100 | 2450 mPas/65–70° C. | highly viscous light yellow |
| 2 | 9 | 1 | 99.1 | 3950 mPas/65–70° C. | soft, paste-like yellowish |
| 3 | 10 | 1 | 97 | — | hard, wax-like, yellowish |
| 4 | 12 | 1 | 91.4 | — | hard, white |
| 5 | 20 | 1 | 100 | — | hard, white |

TABLE 2

Oligohydroxycarboxylic acids from glycerol and glycolide

| Example | Reaction Mixture Glycerol mol | Glycolide mol | Quality | Content of free glycolic acid, % by weight |
| --- | --- | --- | --- | --- |
| 6 | 1 | 4 | soft, wax-like | 0.05% |
| 7 | 1 | 4.5 | hard, barely wax-like | — |
| 8 | 1 | 5 | very hard, not wax-like | — |

TABLE 3

Oligohydroxycarboxylic acids from glycerol and lactide

| Example | Reaction Mixture Glycerol mol | Lactide mol | Quality | Viscosity at measuring temperature | Content of free glycolic acid, % by weight |
| --- | --- | --- | --- | --- | --- |
| 9 | 1 | 2 | viscous, clear | 200 mPAS/65–70° C. | — |
| 10 | 1 | 3 | highly viscous, clear | 850 mPAS/65–70° C. | — |
| 11 | 1 | 4 | soft, clear | 2300 mPAS/65–70° C. | — |
| 12 | 1 | 5 | soft, clear | 2500 mPAS/65–70° C. | 0.125% |
| 13 | 1 | 6 | hard, formable, clear | 4750 mPAS/65–70° C. | 0.075% |
| 14 | 1 | 8 | solid, brittle, clear | 6000 mPAS/65–70° C. | — |
| 15 | 1 | 10 | solid, brittle, clear | 14000 mPAS/65–70° C. | — |
| 16 | 1 | 20 | solid, brittle, | cannot be measured | — |

TABLE 3-continued

Oligohydroxycarboxylic acids from glycerol and lactide

| Example | Reaction Mixture Glycerol mol | Lactide mol | Quality | Viscosity at measuring temperature | Content of free glycolic acid, % by weight |
|---|---|---|---|---|---|
| | | | clear | | |

Examples 17 to 19

Purification of the Waxy Oligomer Reaction Product to Isolate Bone Waxes

To remove free glycolic acid and other low molecular weight consitutents, the reaction products of Examples 2 to 4 were purified by reprecipitation.

Procedure

The waxy oligomer reaction products of Examples 2 to 4 based on glycolic acid were suspended in the same quantity by volume of acetone and then precipitated dropwise into 10 times the quantity of isopropanol. Isolation was followed by drying in a vacuum drying cabinet for 24 hours at 50° C.

TABLE 4

| Example | Unpurified wax of Example No. | Yield after drying % by weight | Appearance of Product | Free glycolic acid |
|---|---|---|---|---|
| 17 | 2 | 22.2% | a soft paste, | 0.04 |
| 18 | 3 | 78% | formable, wax-like | — |
| 19 | 4 | 66% | barely wax-like, hard | |

We claim:

1. A composition for mechanical blood coagulation on hard body tissue which comprises: a resorbable body and tissue compatible wax which is viscous to solid at body temperatures consisting essentially of a blood coagulation effective amount of a polyester oligomer, of at least one hydroxycarboxylic acid of the formula

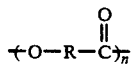

wherein R is a straight chain alkyl group, a branched chain alkyl group, an unsubstituted cycloalkyl group, an alkyl substituted cycloalkyl group, an unsubstituted phenyl group or an alkyl substituted phenyl group each having from 1 to 20 carbon atoms, n is a number selected so that the oligomer has a mean molecular weight of from about 200 to about 1500, containing less than about 0.1% by weight of free hydroxycarboxylic acid, and having at least one co-reactant moiety bound thereto in a terminal position wherein said co-reactant moiety comprises a physiologically, compatible trihydroxy alcohol having from 3 to 21 carbon atoms.

2. The composition of claim 1 wherein said polyester oligomer has an average molecular weight of from about 300 to 1000.

3. The composition of claim 1 wherein said resorbable wax is soft spreading at temperatures between body temperature and when heated briefly up to about 100° c.

4. The composition of claim 1 wherein said resorbable wax is soft spreading at temperatures between body temperature and when heated briefly up to about 60° C.

5. The composition of claim 1 wherein said at least one hydroxycarboxylic acid comprises lactic acid or glycolic acid.

6. The composition of claim 1 where said physiologically compatible trihydroxy alcohol is glycerol.

7. A composition for mechanical blood coagulation on hard body tissue which comprises: a resorbable body and tissue compatible wax which is viscous to solid at body temperatures and which is effective in the coagulation of blood on hard body tissue consisting essentially of a polyester oligomer of at least one of lactic and glycolic acid, containing less than about 0.1% by weight of free hydroxycarboxylic acid, and having glycerol in a terminal position.

8. A method for blood coagulation on endogenous hard body tissue which comprises: applying to said hard body tissue a resorbable body and tissue compatible and spreadable wax comprising a blood coagulation effective amount of a polyester oligomer of at least one hydroxycarboxylic acid of the formula

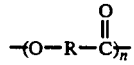

wherein R is a straight chain alkyl group, a branched chain alkyl group, an unsubstituted cycloalkyl group, an alkyl substituted cycloalkyl group, an unsubstituted phenyl group or an alkyl substituted phenyl group each having from 1 to 20 carbon atoms, n is a number selected so that the oligomer has a mean molecular weight of from about 200 to about 1500, containing less than about 0.1% by weight of free hydroxycarboxylic acid, and having at least one co-reactant moiety bound thereto in a terminal position wherein said co-reactant comprises a physiologically compatible trihydroxy alcohol having from 3 to 21 carbon atoms.

9. The method of claim 8 wherein said wax consist essentially of a polyester oligomer of at least one of lactic and glycolic acid having at least one co-reactant moiety bound thereto in a terminal position wherein said co-reactant comprises glycerol.

10. A process for the production of a resorbable body and tissue compatible wax which is viscous to solid at body temperature which comprises:

a) reacting a hydroxycarboxylic acid of the formula

wherein R is a straight chain alkyl group, a branched chain alkyl group, an unsubstituted cycloalkyl group, an alkyl substituted cycloalkyl group, an unsubstituted phenyl group or an alkyl substituted phenyl group each having from 1 to 20 carbon atoms, n is a number selected so that the oligomer has a mean molecular weight of from about 200 to about 1500 and a physiologically compatible trihydroxy alcohol having from 3 to 21 carbon atoms to provide a mixture containing a polyester oligomer having an average molecular weight between about 200 and about 1500 and unreacted hydroxycarboxylic acid;

b) contacting the mixture with an organic solvent for the unreacted hydroxycarboxylic acid in which the polyesteroligomer is essentially insoluble;

c) separating the wax from the organic solvent.

11. The process of claim 10 wherein said organic solvent comprises isopropanol.

12. A process of claim 10 wherein the hydroxycarboxylic acid is at least one of glycolic acid and lactic acid and the trihydoxy alcohol is glycerol.

13. A composition of claim 7 wherein the oligomer is a glycolic acid oligomer wherein the ratio of mols of glycolic acid used to form the oligomer to the number of mols of glycerol is from about 9:1 to about 12:1.

14. A composition of claim 13 wherein the ratio is from about 9:1 to about 10:1.

15. A composition of claim 7 wherein the oligomer is a lactic acid oligomer wherein the ratio of the number of mols of lactic acid used to form the oligomer to the number of mols of glycerol is about 12:1.

16. A composition of claim 7 wherein the oligomer contains moieties from glycolic acid and from lactic acid.

* * * * *